United States Patent
Moore et al.

(10) Patent No.: US 6,511,432 B2
(45) Date of Patent: Jan. 28, 2003

(54) PREAMPLIFIER AND PROTECTION CIRCUIT FOR AN ULTRASOUND CATHETER

(75) Inventors: Thomas C. Moore, Fremont, CA (US); Veijo Suorsa, Sunnyvale, CA (US); Donald Masters, Sunnyvale, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 73 days.

(21) Appl. No.: 09/844,416

(22) Filed: Apr. 27, 2001

(65) Prior Publication Data

US 2001/0016688 A1 Aug. 23, 2001

Related U.S. Application Data

(63) Continuation of application No. 09/290,157, filed on Apr. 12, 1999, now Pat. No. 6,251,098.

(51) Int. Cl.[7] .............................................. A61B 8/00
(52) U.S. Cl. ...................................... 600/459; 600/443
(58) Field of Search ................................ 600/447, 437, 600/443, 459, 448, 449, 460; 128/917

(56) References Cited

U.S. PATENT DOCUMENTS

| | | | | |
|---|---|---|---|---|
| 4,387,722 A | * | 6/1983 | Kearns | ........................ 128/716 |
| 4,674,515 A | | 6/1987 | Andou et al. | |
| 5,125,410 A | | 6/1992 | Misono et al. | |
| 5,131,397 A | | 7/1992 | Crowley | |
| 5,158,088 A | * | 10/1992 | Nelson et al. | ............... 600/461 |
| 5,271,403 A | | 12/1993 | Paulos | |
| 5,307,815 A | | 5/1994 | Gatzke et al. | |
| 5,329,498 A | | 7/1994 | Greenstein | |
| 5,360,007 A | * | 11/1994 | Shinomura et al. | ......... 600/447 |
| 5,572,487 A | | 11/1996 | Tims | |

FOREIGN PATENT DOCUMENTS

| | | |
|---|---|---|
| EP | 0 659 387 A2 | 6/1995 |
| JP | 57 191579 | 11/1982 |
| JP | 06 217980 | 8/1994 |

* cited by examiner

*Primary Examiner*—Francis J. Jaworski
*Assistant Examiner*—Maulin Patel
(74) *Attorney, Agent, or Firm*—Orrick, Herrington & Sutcliffe LLP

(57) ABSTRACT

An ultrasound catheter is disclosed wherein a rotatable transducer couples to the input of a preamplifier. Protection circuits at the input and output of the preamplifier protect the preamplifier from the transducer excitation signal. The preamplifier couples to the distal end of a transmission line. In an alternate embodiment, at least one switch responds to the presence of the transducer excitation signal by coupling the transducer excitation signal to the rotatable transducer and protecting the preamplifier from the transducer excitation signal. The at least one switch responds to the absence of the transducer excitation signal by coupling a received signal produced by the rotatable transducer to the input of the preamplifier. The at least one switch further responds to the absence of the transducer excitation signal by coupling the output of the preamplifier to the distal end of the transmission line.

25 Claims, 3 Drawing Sheets

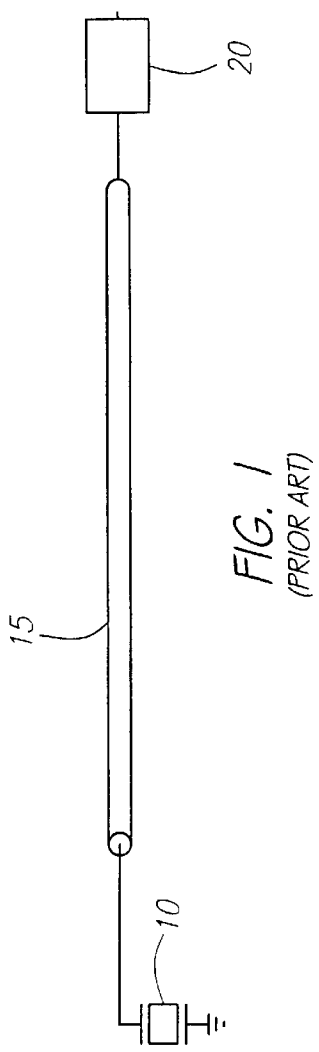
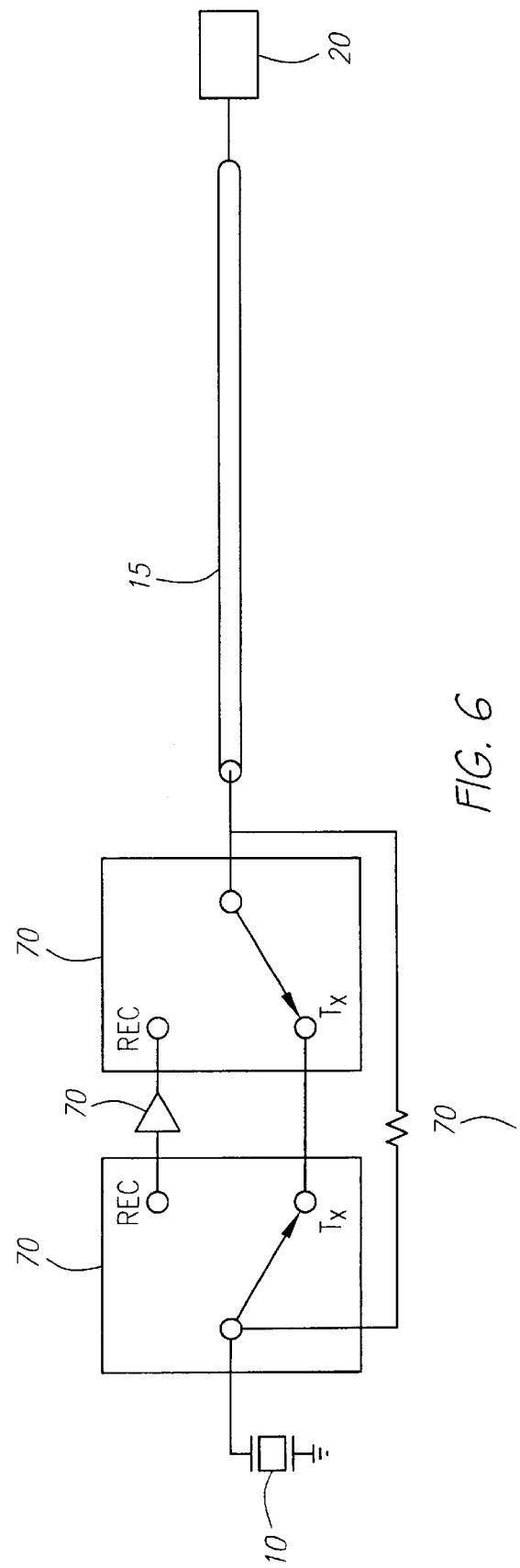

PREAMPLIFIER AND PROTECTION CIRCUIT FOR AN ULTRASOUND CATHETER

CROSS-REFERENCE TO PRIOR APPLICATION

This application is a continuation of U.S. patent application Ser. No. 09/290,157 filed Apr. 12, 1999, now U.S. Pat. No. 6,251,098, which is incorporated herein and made a part hereof by reference.

FIELD OF THE INVENTION

This invention relates to ultrasound systems. More particularly, this invention relates to an ultrasound catheter having a preamplifier and protection circuitry.

BACKGROUND OF THE INVENTION

Intravascular ultrasound systems allow clinicians to image within coronary arteries and other vessels. Typically, the clinician will route a guidewire from the femoral artery, through the aorta and into the coronary arteries. When satisfied with the location of the guidewire, the clinician guides an ultrasound catheter having a transmission line coupled to a rotating transducer at its distal end along the guidewire to the coronary arteries. As illustrated in FIG. 1, signals produced by the transducer 10 must travel through the transmission line 15 before being processed in the signal processor 20. Because the signals are of small amplitude and must travel through 5 to 6 feet of transmission line before being processed, noise received during transmission in the transmission line presents a serious problem.

In addition to the noise added by the transmission line, intravascular ultrasound systems face other problems. For example, because the transducer typically comprises a resonant piezoelectric structure, the impedance of the transducer has a significant capacitive component. The efficiency and bandwidth of the transducer are raised if the impedance of the transducer is "tuned" by adding, for example, an inductive component to cancel the imaginary component of the transducer impedance. A wider bandwidth enables a shorter ultrasound pulse width, thus improving image resolution. In addition, the transducer should be impedance matched to the characteristic impedance of the transmission line for maximum performance.

There is a need in the art for improved intravascular ultrasound systems which reduce the effect of noise added from the transmission line and which ease the tuning and matching of the transducer to the transmission line. A preamplifier located adjacent to the rotating transducer and distally to the transmission line increases the amplitude of the transducer signal, lessening the effect of noise. Moreover, the use of such a preamplifier reduces the need for tuning and eases matching of the transducer impedance. Because a preamplifier located adjacent to the transducer will be exposed to high amplitude electric pulses used to excite the transducer, such a preamplifier should be protected with circuitry which prevents the preamplifier from being damaged from these excitations.

Prior art ultrasound systems with rotatable transducers have failed to address the problem caused by the transmission line noise. For example, Andou et al., U.S. Pat. No. 4,674,515 disclose an endoscopic ultrasound system with a rotatable transducer located at the distal end of a transmission line. Although the system disclosed by Andou et al. possesses a preamplifier, this preamplifier is located at the proximal end of the cable so that it cannot improve the signal-to-noise ratio before signal transmission through the transmission line. In addition, a proximally located preamplifier does not simplify tuning or matching of the transducer impedance.

SUMMARY OF THE INVENTION

In one innovative aspect, the present invention comprises an ultrasound catheter having a rotatable transducer distally coupled to a transmission line. A preamplifier is distally coupled to the transmission line and coupled to the rotatable transducer. Protection circuitry protects the input and output of the preamplifier from high amplitude electrical impulses (the transducer excitation signal) used to excite the rotatable transducer. The protection circuitry may comprise either back-to-back diodes or diode bridges. Alternatively, the protection circuitry may comprise at least one GaAs switch. In a preferred embodiment, the at least one GaAs switch comprises two GaAs switches coupled to the input and output of the preamplifier, respectively. Each GaAs switch may comprise a double pole single throw switch wherein the switches are switchable between a transmit path which bypasses the preamplifier and a receive path which couples to the preamplifier. The GaAs switches are responsive to the transducer excitation signal, switching to the transmit path when the transducer excitation signal is present and switching to the receive path when the transducer excitation signal is absent.

Preferably, the output impedance of the preamplifier matches the characteristic impedance of the transmission line. In addition, tuning circuitry is preferably coupled to the rotatable transducer to reduce the imaginary component of the impedance of the transducer, thus increasing the efficiency and bandwidth of the transducer.

In one embodiment of the present invention, a DC power signal is multiplexed with the transducer excitation signal on the transmission line. The preamplifier receives the DC power signal through an inductor, which blocks the transducer excitation signal. Similarly, the transducer receives the transducer excitation signal through a capacitor, which blocks the DC power signal. If diode bridges are used as the protection circuitry for the preamplifier, the diode bridges are coupled to the power signal to provide a required diode bridge bias voltage.

In another embodiment of the present invention, a drive cable outside of the transmission line carries the DC power signal. The preamplifier and, if used, the diode bridges are coupled to the drive cable to receive the DC power signal.

In yet another embodiment of the present invention, no external DC power signal is provided to the preamplifier. Instead, a rectification circuit adjacent to the preamplifier rectifies the transducer excitation signal to produce the DC power signal.

DESCRIPTION OF THE DRAWINGS

FIG. 1 is a block diagram of a prior art intravascular ultrasound system.

FIG. 6 is a block diagram of an ultrasound catheter using GaAs switches according to one embodiment of the invention.

DETAILED DESCRIPTION OF THE INVENTION

Figure 2:
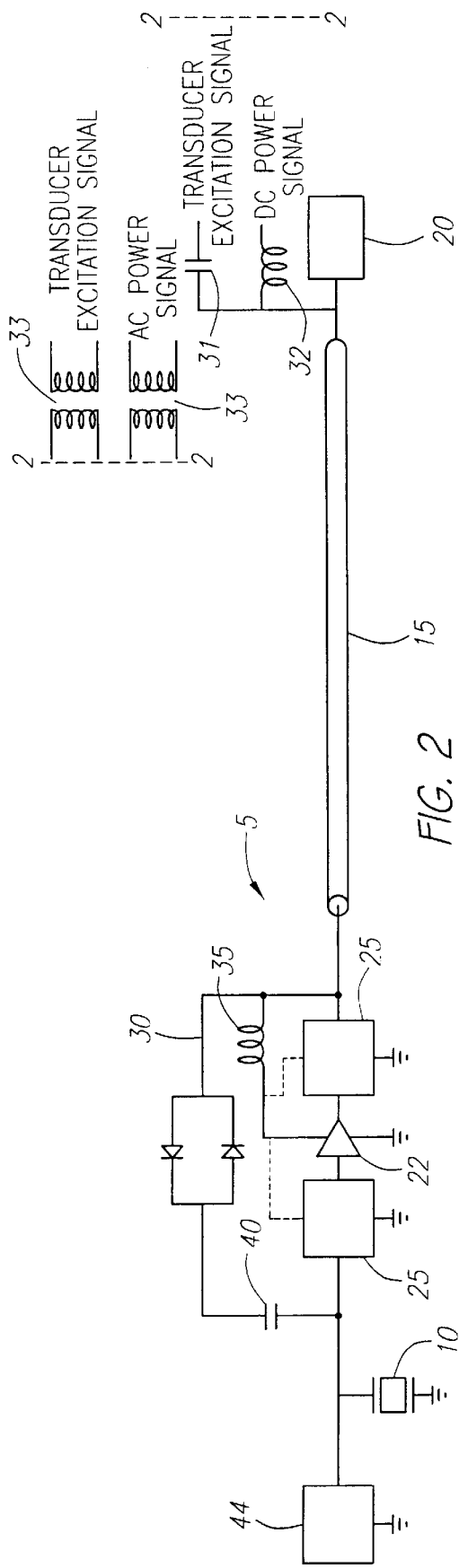
FIG. 2 is a block diagram of an ultrasound catheter according to one embodiment of the invention.

Turning now to FIG. 2, a rotatable transducer 10 couples to the distal end of a transmission line 15 in an ultrasound catheter 5. The transmission line 15 may comprise a coaxial cable, a twisted-wire pair or other suitable means. A preamplifier 22, also coupled to the distal end of the transmission line 15, amplifies a received signal produced by the rotatable transducer 10. Note that the preamplifier 22 will need a DC power signal for proper operation whereas the rotatable transducer requires a transducer excitation signal consisting of, in one embodiment, bipolar high amplitude impulses. The transmission line provides only a single channel for signal transmission. Thus, the ultrasound catheter 5 of the present invention includes three different embodiments in which the two separate signals, the DC power signal and the transducer excitation signal are accommodated. In the first embodiment, illustrated in FIG. 2, the transducer excitation signal and the DC power signal are multiplexed onto the transmission line 15. At the proximal end of the transmission line 15, each signal is coupled through rotary transformers 33. Note that the rotary transformer 33 is coupled to an AC power signal. This AC power signal 1 is rectified (using well-known techniques) on the rotating side of the rotary transformer 33 to produce the DC power signal. The transducer excitation signal then couples to the transmission line 15 through a blocking capacitor 31, which blocks transmission of the DC power signal. Similarly, the DC power signal couples to the transmission line 15 through blocking inductor 32, which blocks transmission of the transducer excitation signal. Distal to the transmission line 15, the signals are demultiplexed analogously. Thus, a blocking inductor 35 transmits the DC power signal to the preamplifier 22 while blocking transmission of the transducer excitation signal, and a blocking capacitor 40 transmits the alternating transducer excitation signal to the rotatable transducer 10 while blocking transmission of the DC power signal.

Figure 3:
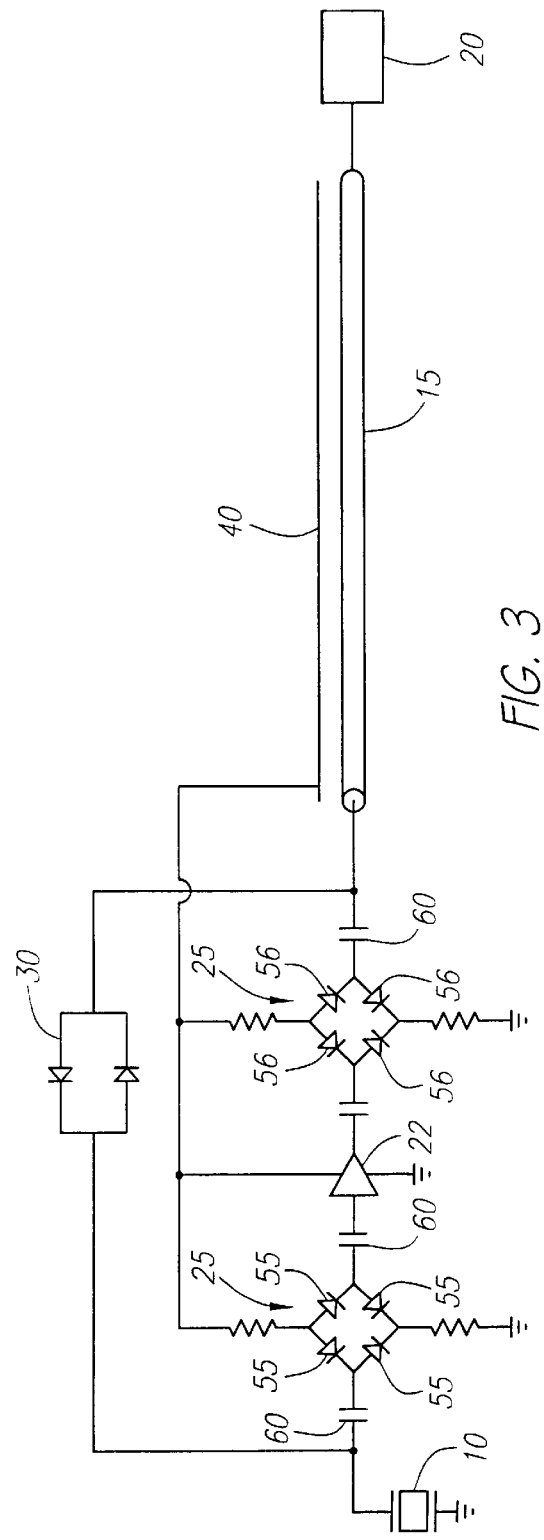
FIG. 3 is a block diagram of an ultrasound catheter having an external DC power supply and protection circuitry comprising diode bridges according to one embodiment of the invention.

In a second embodiment, illustrated in FIG. 3, the transducer excitation signal and the DC power signal are not multiplexed onto the transmission line 15. Instead, the transmission line 15 carries only the transducer excitation signal and received echo signals. The DC power signal transmits through an external drive cable 40. As illustrated, the external drive cable 40 may consist of only a single conductor so it shares the outer conductor of transmission line as its ground, or it may have its own ground. The preamplifier 22 couples to the external drive cable 40 to provide the DC power signal. The rotatable transducer 10 couples to the transmission line 15 to receive the transducer excitation signal.

Figure 4:
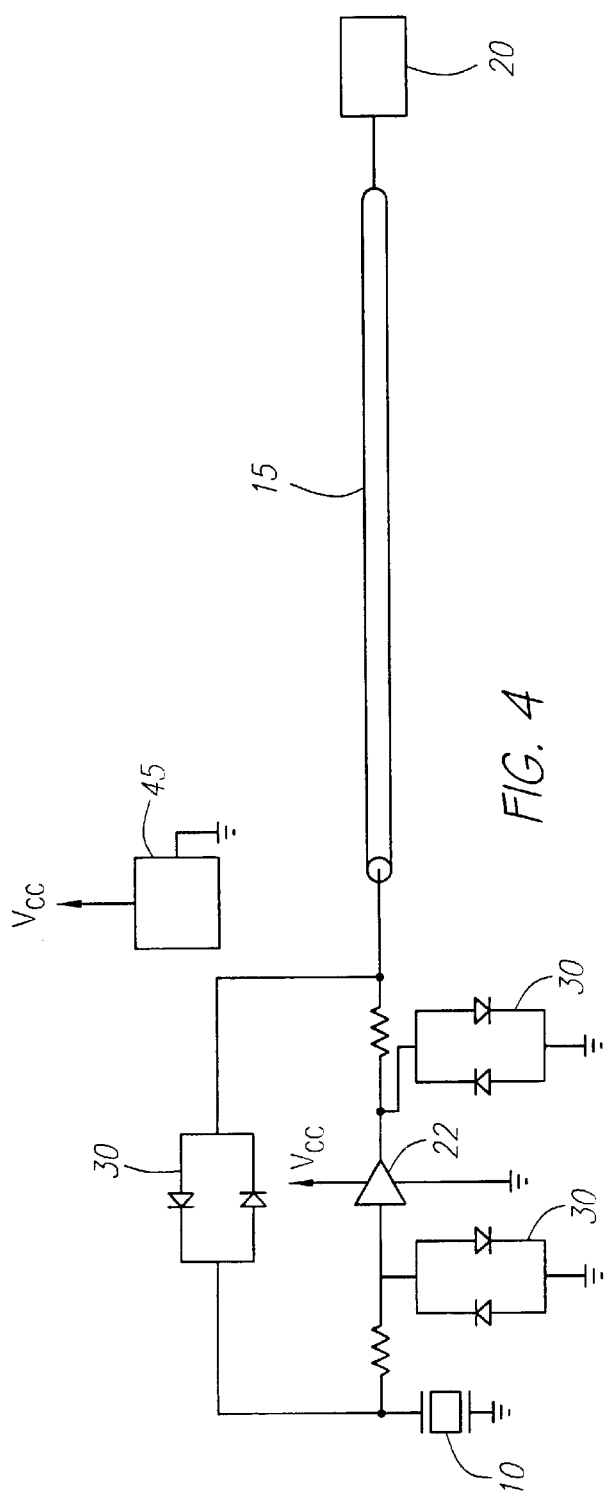
FIG. 4 is a block diagram of an ultrasound catheter having a rectification circuit providing a DC power supply for a preamplifier according to one embodiment of the invention.
Figure 5:
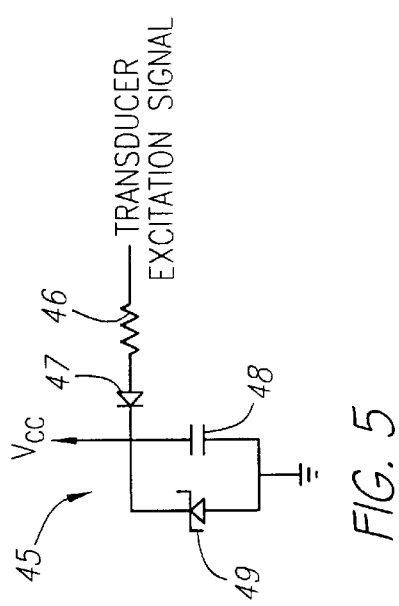
FIG. 5 is a schematic diagram of a rectification circuit according to one embodiment of the invention.

In a third embodiment, illustrated in FIG. 4, a DC power signal is not externally supplied through a drive cable 40 or through multiplexing onto the transmission line 15. Instead, the ultrasound catheter 5 generates the DC power signal through rectification of the transducer excitation signal in a rectifier circuit 45. The rectifier circuit 45 preferably couples to the transducer excitation signal at the output of the preamplifier 22 to assure the strongest signal possible for rectification. A suitable rectifier circuit 45, illustrated in FIG. 5, comprises a series connected resistor 46, diode 47 and capacitor 48. The rectified DC power signal, denoted as Vcc, is stored across the capacitor 48. A zener diode 49, arranged in parallel with the capacitor 48, regulates the DC power signal. Those of ordinary skill in the art will appreciate that many alternate circuits could be constructed to perform similarly to the circuit illustrated in FIG. 5.

The preamplifier 22 receives the DC power signal and amplifies the received signals produced by the rotatable transducer 10. The transducer excitation signal may consist of voltage impulses of up to +/−50 volts. Such voltage spikes could easily damage the preamplifier 22. Thus, the present invention preferably has protection circuits 25 at both the input and the output of the preamplifier 22 to prevent transmission of the transducer excitation signal into the preamplifier 22. An alternative embodiment, employing a GaAs switch to protect the preamplifier 22, illustrated in FIG. 6, will be discussed below.

The present invention contemplates two types of protection circuits 25, biased and unbiased. If the protection circuits are biased, they require a lead to the DC power signal, an illustrated by the dotted line in FIG. 2. Turning now to FIG. 3, one type of biased protection circuit 25 comprises diode bridges 25. The biased form of a suitable protection circuit 25 is illustrated in FIG. 3. Diodes 55 protect the input of preamplifier 22 from the transducer excitation signal. As illustrated, the diodes 55 are biased with the DC power signal obtained from the drive cable 40. However, the DC power signal could alternatively be supplied in the multiplexing or the rectification embodiments discussed above. Diodes 55, while blocking the transducer excitation signal, will transmit small amplitude received signals generated by rotating transducer 10 because, being biased, the diodes 55 are all in the on-state and thus have a relatively small resistance.

Similarly, diodes 56 protect the output of preamplifier 22 from the transducer excitation signals. Diodes 56 also are biased with the DC power signal obtained from the drive cable 40. Diodes 56 will pass the amplified received signal produced by preamplifier 22 because, although the received signals are amplified, they are still below the cutoff voltage (typically +/−0.7 volts) of the diodes 56. Blocking capacitors 60 provide isolation between the input and outputs of the diode bridges 25.

A pair of back-to-back diodes 30, arranged in parallel, is included in the embodiments-illustrated in FIGS. 2 and 3. The transducer excitation signal, which preferably is bipolar, will pass alternatively though one of the pair of back-to-back diodes 30, depending on the positive or negative charge of the biphase transducer excitation signal. However, the back-to-back diodes 30 will not transmit the small amplitude received signal produced by the rotatable transducer 10, thus providing useful isolation between the input and output of the preamplifier 22.

The pair of back-to-back diodes 30 may also be used as a form of unbiased protection circuits 25 for protecting the input and output of the preamplifier 22 as illustrated in FIG. 4. Regardless of the polarity of the transducer excitation signal, its high amplitude will cause one of the pair of back-to-back diodes 30 to conduct, shunting the pulse to ground and blocking transmission to the preamplifier 22. Resistors 65 prevent the back-to-back diodes 30 from shunting the transducer excitation signal away from the rotatable transducer 10. Many other unbiased circuits may be used as an alternative to the back-to-back diodes 30.

In addition to the use of protection circuitry 25, the present invention contemplates the use of a GaAs or similarly fast-operating switch to protect the preamplifier 22 from the high amplitude transducer excitation signal as illustrated in FIG. 6. GaAs switches 70 can operate at speeds in excess of 3 to 4 nanoseconds. Thus, such switches 70 are fast enough that they could sense the incoming transducer excitation signal pulse and switch away from the preamplifier input and outputs to prevent damage to the preamplifier. Similarly, GaAs switches would sense the absence of the transducer excitation signal and switch back to the preamplifier 22 input and outputs so that the received signal could be transmitted down the transmission line 15 to the signal processing unit 20.

Many switch configurations are suitable. For example, a double-pole, single-throw switch 70 could be implemented at the input and the output of the preamplifier 22. Note that the embodiment illustrated in FIG. 6 would require a DC power signal (not illustrated) supplied through, as discussed previously, for example, an external drive cable 40. The DC power signal would then supply the GaAs switches 70 and the preamplifier 22 with operating power. The GaAs switch 70 located at the output of the preamplifier 22 directly couples to the transmission line 15 and thus may sense an incoming transducer excitation signal. The GaAs switch 70 located at the input to the preamplifier 22 is not directly coupled to the transmission line 15. Thus, a control signal path with resistor 75 provides a channel for transmission of an incoming transducer excitation signal to this GaAs switch 70. Should either switch 70 sense an incoming transducer excitation signal, the switches 70 switch to the transmission pole (denoted Tx). In this fashion, the transducer excitation signal may flow though the switches 70 to the rotatable transducer 10. If the switches 70 sense the absence of a transducer excitation signal, the switches 70 switch to the receive pole (denoted Rec). In such a state, the received signal generated by the rotatable transducer transmits through the preamplifier 22 and into the transmission line 15 for processing in signal processing unit 20 (note that FIG. 6 illustrates the switches in the transmit state only).

The rotatable transducer 10 typically comprises a piezoelectric element. Although such transducers operate as resonant structures, the appreciable capacitive component within the impedance of a piezoelectric element lowers the achievable efficiency and bandwidth. Canceling out this capacitive (and hence imaginary) impedance through a tuning circuit 44 as illustrated in FIG. 2 improves the efficiency and bandwidth of the system. Use of such tuning circuits improves the resolution of the ultrasound imaging system because narrower ultrasound pulses may be produced. Tuning circuit 44 may comprise a suitable inductor which cancels the capacitive component of the transducer impedance. Although arranged in parallel with the transducer 10 in the embodiment illustrated in FIG. 2, a tuning circuit 44 may be used in series or in parallel with the transducer 10 in any embodiment of the present invention.

The present invention, by coupling a preamplifier 22 to the rotatable transducer 10 distally to the transmission line 15 provides a number of advantages. Consider the prior art ultrasound catheter 5 illustrated in FIG. 1. The rotatable transducer 10 typically has a capacitance under 100 pF. On the other hand, the transmission line 15, which is at least 5 to 6 feet in length, has a total capacitance of approximately 150 to 250 pF. This capacitive loading lowers the achievable signal-to-noise ratio at the signal processing unit 20. However, if the transmission line 15 is coupled to the preamplifier 22 instead of directly to the rotatable transducer as in the present invention, the transmission line 15 "sees" only the output impedance of the preamplifier 22. Conventionally, the transmission line 15 is a 50 Ω line, an impedance easily matched by commercially available preamplifiers. Thus, the present invention alleviates the impedance mismatch between conventional rotatable transducers 10 and transmission lines 15. Moreover, the present invention reduces the need for a tuning circuit 44. Consider the embodiments illustrated in FIGS. 3, 4, and 6 in which the tuning circuit 44 is absent. Although in these embodiments there will be an impedance mismatch between the input of the preamplifier 22 and the rotatable transducer 10, the reflected wave effects of such a mismatch is minimized because the preamplifier is adjacent (in a transmission line sense with respect to the ultrasound frequency and wavelengths in consideration) the rotatable transducer 10.

While the invention is susceptible to various modifications, and alternative forms, specific examples thereof have been shown in the drawings and are herein described in detail. It should be understood, however, that the invention is not to be limited to the particular forms disclosed, but to the contrary, the invention is to cover all modifications, equivalents and alternatives falling within the spirit and scope of the appended claims.

We claim:

1. An ultrasound catheter for imaging tissue within a body, the ultrasound catheter comprising:
    a transmission line having a distal end;
    a rotatable transducer responsive to a transducer excitation signal from the transmission line, the rotatable transducer generating a first signal representative of data about body tissue;
    a preamplifier having an input and output;
    a first protection circuit coupling the rotatable transducer to the input of the preamplifier, the first protection circuit coupling the first signal to the input of the preamplifier and protecting the preamplifier from the transducer excitation signal, wherein the preamplifier generates an amplified first signal; and
    a second protection circuit coupling the output of the preamplifier to the transmission line, the second protection circuit also coupling the amplified first signal produced by the preamplifier to the transmission line and protecting the preamplifier from the transducer excitation signal.

2. The ultrasound catheter of claim 1 wherein the preamplifier is powered by a DC power signal and the DC power signal is multiplexed with the transducer excitation signal on the transmission line.

3. The ultrasound catheter of claim 1 further comprising a drive cable and wherein DC power signal is carried on the drive cable.

4. The ultrasound catheter of claim 1 wherein the first protection circuit and the second protection circuit each comprises a pair of back-to-back diodes arranged in parallel.

5. The ultrasound catheter of claim 1 wherein the first protection circuit and the second protection circuit each comprises a diode bridge.

6. The ultrasound catheter of claim 1 further comprising a tuning circuit coupled to the rotatable transducer.

7. The ultrasound catheter of claim 6 wherein the tuning circuit comprises an inductor which blocks the transducer excitation signal from reaching the preamplifier.

8. The ultrasound catheter of claim 1 further comprising a rectification circuit coupled to the transmission line, wherein the rectification circuit rectifies the transducer excitation signal to produce a DC power signal, the DC power signal providing power to the preamplifier.

9. The ultrasound catheter of claim 8 wherein the rectification circuit comprises a diode and capacitor arranged in series, wherein the DC power signal is produced across the capacitor and the capacitor blocks the DC power signal from reaching the rotatable transducer.

10. The ultrasound catheter of claim 9 wherein the rectification circuit further comprises a zener diode arranged in parallel with the capacitor.

11. The ultrasound catheter of claim 1 further comprising a pair of back-to-back diodes arranged in parallel, the back-to-back diodes coupling the rotatable transducer to the distal end of the transmission line.

12. The ultrasound catheter of claim 1 wherein the preamplifier is located near the distal end of the transmission line.

13. An ultrasound catheter for imaging tissue within a body, the ultrasound catheter comprising:
   a transmission line having a distal end;
   a rotatable transducer responsive to a transducer excitation signal carried on the transmission line, the rotatable transducer generating a first signal representative of data about body tissue;
   a preamplifier having an input and an output;
   at least one switch coupled to the distal end of the transmission line, the at least one switch responsive to the presence and absence of the transducer excitation signal, wherein the at least one switch responds to the presence of the transducer excitation signal by coupling the transducer excitation signal to the rotatable transducer while isolating the input and output of the preamplifier from the transducer excitation signal, and wherein the at least one switch responds to the absence of the transducer excitation signal by coupling the input of the preamplifier to the rotatable transducer and by coupling the output of the preamplifier to the distal end of the transmission line.

14. The ultrasound catheter of claim 13 wherein the at least one switch comprises a GaAs switch.

15. The ultrasound catheter of claim 13 wherein the at least one switch comprises at least two switches.

16. The ultrasound catheter of claim 15 wherein the at least two switches are GaAs switches.

17. The ultrasound catheter of claim 14 wherein the at least one switch comprises:
   a first switch coupled to the distal end of the transmission line and comprising a double pole single throw, wherein one pole of the first switch couples to the output of the preamplifier and the other pole of the first switch couples to a preamplifier bypass path, and wherein the first switch switches to the other pole in response to the presence of the transducer excitation signal, and wherein the first switch switches to the one pole in response to the absence of the transducer excitation signal;
   a second switch couples to the distal end of the transmission line and comprising a double pole single throw switch, wherein one pole of the second switch couples to the input of the preamplifier and the other pole of the second switch couples to the preamplifier bypass path, and wherein the second switch switches to the one pole in response to the absence of the transducer excitation signal, and wherein the second switch switches to the other pole in the presence of the transducer excitation signal.

18. The ultrasound catheter of claim 13 wherein the preamplifier is powered by a DC power signal and the DC power signal is multiplexed with the transducer excitation signal on the transmission line.

19. The ultrasound catheter of claim 13 further comprising a drive cable and wherein DC power signal is carried on the drive cable.

20. The ultrasound catheter of claim 13 further comprising a tuning circuit coupled to the rotatable transducer.

21. The ultrasound catheter of claim 20 wherein the tuning circuit comprises an inductor which blocks the transducer excitation signal from reaching the preamplifier.

22. The ultrasound catheter of claim 13 further comprising a rectification circuit coupled to the transmission line, wherein the rectification circuit rectifies the transducer excitation signal to produce a DC power signal, the DC power signal providing power to the preamplifier.

23. The ultrasound catheter of claim 22 wherein the rectification circuit comprises a diode and capacitor arranged in series, wherein the DC power signal is produced across the capacitor and the capacitor blocks the DC power signal from reaching the rotatable transducer.

24. The ultrasound catheter of claim 23 wherein the rectification circuit further comprises a zener diode arranged in parallel with the capacitor.

25. The ultrasound catheter of claim 13 wherein the preamplifier is located near the distal end of the transmission line.

* * * * *